US00PP33850P2

(12) United States Plant Patent
Heuger

(10) Patent No.: US PP33,850 P2
(45) Date of Patent: Jan. 11, 2022

(54) ***SAXIFRAGA* PLANT NAMED 'SH 1933'**

(50) Latin Name: *Saxifraga cortusifolia*
Varietal Denomination: SH 1933

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 17/178,011

(22) Filed: Feb. 17, 2021

(51) Int. Cl.
*A01H 5/02* (2018.01)
*A01H 6/80* (2018.01)
*A01H 5/10* (2018.01)

(52) U.S. Cl.
USPC ..... Plt./263.1
CPC ..... *A01H 6/80* (2018.05); *A01H 5/02* (2013.01); *A01H 5/10* (2013.01)

(58) Field of Classification Search
USPC ..... Plt./263.1
See application file for complete search history.

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct cultivar of *Saxifraga* plant named 'SH 1933', characterized by its upright to outwardly spreading and mounded plant habit; moderately vigorous growth habit; dark green-colored leaves; and numerous red purple-colored flowers held about the foliar plane.

2 Drawing Sheets

Figure 1:
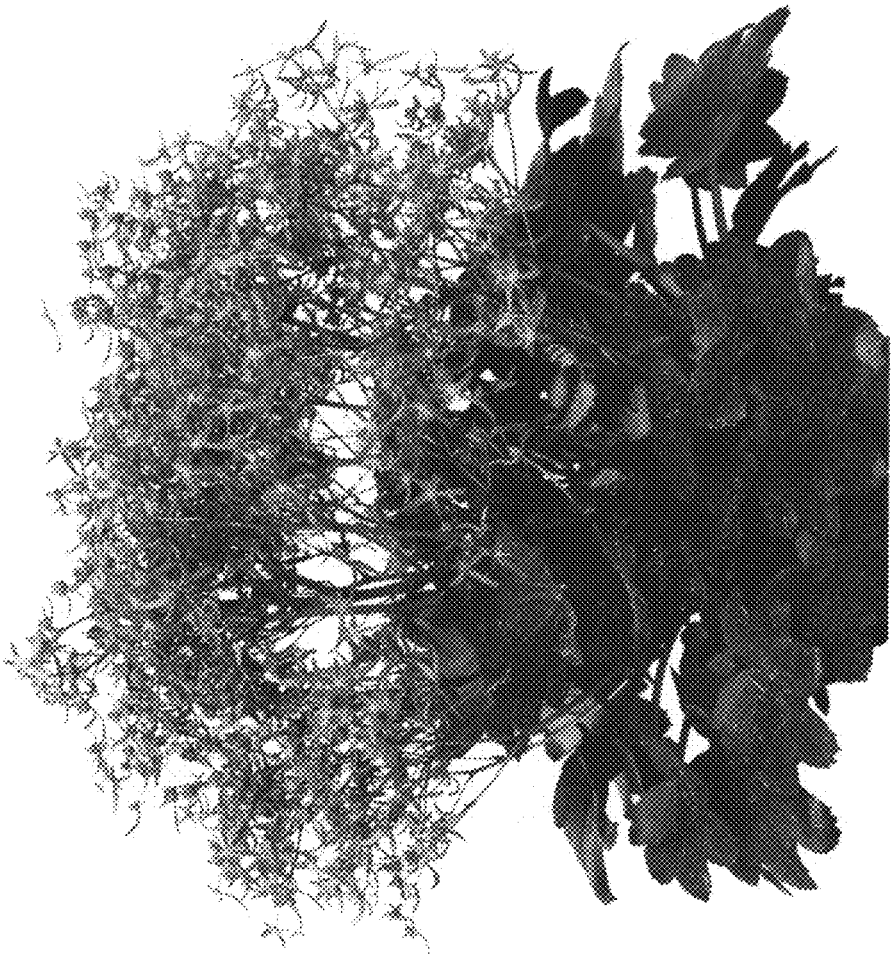

Botanical designation: *Saxifraga cortusifolia.*
Cultivar denomination: 'SH 1933'.

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Nov. 30, 2020, application number 2020/3087. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Saxifraga* plant, botanically known as *Saxifraga cortusifolia* and hereinafter referred to by the name 'SH 1933'.

The new *Saxifraga* plant is a product of a planned breeding program conducted by the Inventor in Glandorf, Germany. The objective of the breeding program was to create new uniform *Saxifraga* plants with unique and attractive plant habit, leaf and flower coloration.

The new *Saxifraga* plant originated from a cross-pollination conducted by the Inventor in Glandorf, Germany in October, 2014 of a proprietary selection of *Saxifraga cortusifolia* identified as code number 16-423, not patented, as the female, or seed patent and a proprietary selection of *Saxifraga cortusifolia* identified as code number 15-098, not patented, as the male, or pollen parent. The new *Saxifraga* plant was discovered and selected by the Inventor as a single flowering plant from within the progeny of the stated cross-pollination grown in a controlled greenhouse environment in Glandorf, Germany in October, 2015.

Asexual reproduction of the new *Saxifraga* plant by in vitro axillary meristem culture in a controlled environment in Glandorf, Germany since May, 2016 has shown that the unique features of this new *Saxifraga* plant are stable and reproduced true to type in successive generations.

SUMMARY OF THE INVENTION

Plants of the new *Saxifraga* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SH 1933'. These characteristics in combination distinguish 'SH 1933' as a new and distinct *Saxifraga* plant:

1. Upright to outwardly spreading and mounded plant habit.
2. Moderately vigorous growth habit.
3. Dark green-colored leaves.
4. Freely flowering habit.
5. Red purple-colored flowers held above the foliar plane.

Plants of the new *Saxifraga* differ from plants of the female parent selection in the following characteristics:

1. Leaves of plants of the new *Saxifraga* are darker green in color than leaves of plants of the female parent selection.
2. Flowers of plants of the new *Saxifraga* are red purple in color whereas flowers of plants of the female parent selection are red in color.

Plants of the new *Saxifraga* differ from plants of the male parent selection in the following characteristics:

1. Leaves of plants of the new *Saxifraga* are dark green in color whereas leaves of plants of the male parent selection are red in color.
2. Flowers of plants of the new *Saxifraga* are red purple in color whereas flowers of plants of the male parent selection are red in color.

Plants of the new *Saxifraga* can be compared to plants of *Saxifraga cortusifolia* 'SH 1925', not patented. Plants of the new *Saxifraga* differ primarily from plants of 'SH 1925' in the following characteristics:

1. Leaves of plants of the new *Saxifraga* are lighter green in color than leaves of plants of 'SH 1925'.
2. Flowers of plants of the new *Saxifraga* are red purple in color whereas flowers of plants of 'SH 1925' are pink in color.

BRIEF DESCRIPTION OF THE PHOTOGRAPHS

The accompanying colored photographs illustrate the overall appearance of the new *Saxifraga* plant showing the colors as true as it is reasonably possible to obtain in colored reproductions of this type. Colors in the photographs may differ slightly from the color values cited in the detailed botanical description which accurately describe the colors of the new *Saxifraga* plant.

The photograph on the first sheet (FIG. 1) is a side perspective view of a typical flowering plant of 'SH 1933' grown in a container.

Figure 2:
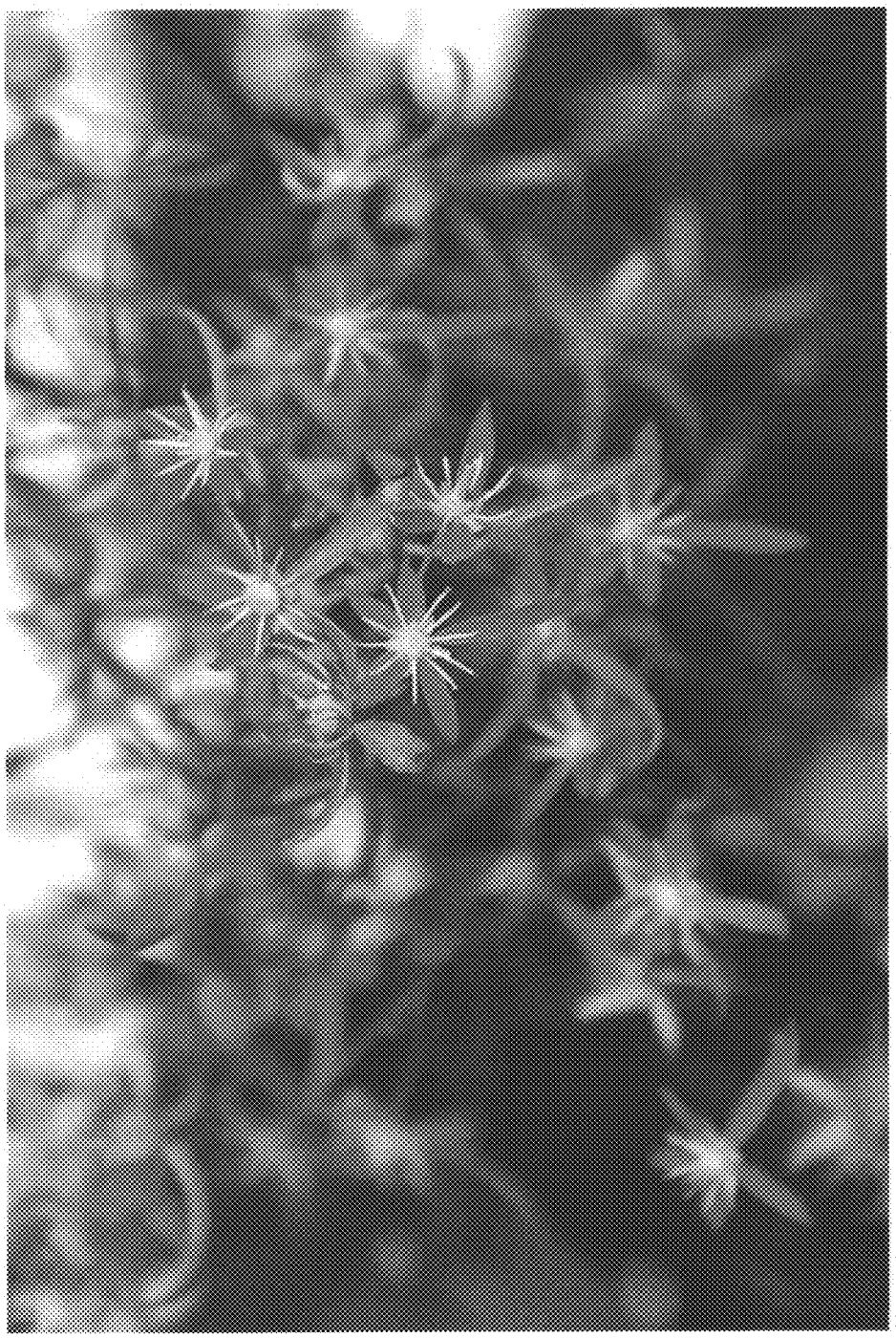

The photograph on the second sheet (FIG. 2) is a close-up view of a typical flowering plant of 'SH 1933'.

DETAILED BOTANICAL DESCRIPTION

The aforementioned photographs and following observations, measurements and values describe plants grown during the summer and autumn in 10.5-cm containers in a glass-covered greenhouse in Glandorf, Germany and under cultural practices typical of commercial *Saxifraga* production. During the production of the plants, day temperatures ranged from 18° C. to 28° C. and night temperatures ranged from 14° C. to 20° C. Plants were six months old when the photographs and the description were taken. In the following description, color references are made to The Royal Horticultural Society Colour Chart, 2015 Edition, except where general terms of ordinary dictionary significance are used.

Botanical classification: *Saxifraga cortusifolia* 'SH 1933'.

Parentage:

*Female, or seed, parent*.—Proprietary selection of *Saxifraga cortusifolia* disclosed as code number 16-423, not patented.

*Male, or pollen, parent*.—Proprietary selection of *Saxifraga cortusifolia* disclosed as code number 15-098, not patented.

Propagation:

*Type*.—In vitro axillary meristem culture.

*Time to produce a rooted young plant in vitro*.—About 36 to 42 days at temperatures about 22° C. to 24° C.

*Root description*.—Fine, fibrous; typically white to brown in color, actual color of the roots is dependent on substrate composition, water quality, fertilizer type and formulation, substrate temperature and physiological age of roots.

*Rooting habit*.—Moderately freely branching; sparse to medium density.

Plant description:

*Plant and growth habit*.—Herbaceous perennial; upright to outwardly spreading and mounding plant habit with flowers held above the foliar plane; overall plant shape, broadly inverted triangular; moderately vigorous growth habit and moderate growth rate.

*Plant height, soil level to top of foliar plane*.—About 12.8 cm.

*Plant height, soil level to top of floral plane*.—About 24.7 cm.

*Plant diameter* (*area of spread*).—About 30.3 cm.

Leaf description:

*Arrangement*.—Leaves arranged in a basal rosette; alternate and single.

*Length*.—About 6.4 cm.

*Width*.—About 8.8 cm.

*Shape*.—Reniform in outline.

*Apex*.—Abruptly acute.

*Base*.—Truncate to shallowly hastate, lobes free.

*Margin*.—Senate and palmately lobed with about seven or occasionally nine lobes per leaf; sinuses shallow to medium in depth and divergent.

*Texture and luster, upper surface*.—Moderately pubescent; slightly glossy.

*Texture and luster, lower surface*.—Sparsely pubescent; moderately glossy.

*Venation pattern*.—Pinnate.

*Color*.—Developing leaves, upper surface: Darker than 147A; narrow margin, close to 200A to 200B. Developing leaves, lower surface: Close to 147C; narrow margin, close to N186C. Fully developed leaves, upper surface: Darker than between 147A and N189A; lobes, tinged with close to between 200A and 203A; venation, darker than between 147A and N189A and lobes, tinged with between 200A and 203A. Fully developed leaves, lower surface: Close to 147C; lobes, tinged with close to 176B and 183C; narrow margin, close to 203A; venation, close to 148C and lobes, tinged with close to 183B.

*Petioles*.—Length: About 10.4 cm. Diameter: About 4 mm. Strength: Weak. Texture and luster, upper and lower surfaces: Sparsely pubescent and proximal end, moderately pubescent; moderately glossy. Color, upper surface: Close to 183A; at proximal end, close to 183B. Color, lower surface: Close to between 178A and 183B.

*Stipules*.—To date, stipule development has not been observed on plants of the new *Saxifraga*.

Flower description:

*Flower shape and habit*.—Rotate flowers arranged in terminal compound corymbs; freely flowering habit with about 180 flowers per inflorescence and about 1,800 flowers developing per plant; flowers face mostly upright to slightly outwardly.

*Fragrance*.—Faint; sweet and pleasant.

*Natural flowering season*.—Plants begin flowering about six months after planting; plants flower naturally during the autumn in Germany.

*Flower longevity on the plant*.—About two weeks; flowers persistent.

*Flower buds*.—Length: About 3 mm. Diameter: About 2.5 mm. Shape: Broadly ovate. Texture and luster: Smooth, glabrous; slightly glossy. Color: Petals, close to 63B, and sepals, close to 145A.

*Inflorescence height* (*including peduncle*).—About 22.7 cm.

*Inflorescence diameter*.—About 15.9 cm.

*Flower diameter*.—About 1.5 cm by 2 cm.

*Flower depth* (*height*).—About 7 mm.

*Petals*.—Quantity and arrangement: About five, occasionally six, arranged in a single whorl; upper four petals are smaller than lower one or two petals. Length, upper petals: About 7 mm to 8 mm. Width, upper petals: About 2 mm. Length, lower petals: About 1.4 cm to 2 cm. Width, lower petals: About 2 mm. Shape, upper petals: Narrowly ovate to narrowly elliptic. Shape, lower petals: Narrowly elliptic to narrowly oblanceolate. Apex, upper and lower petals: Acute. Base, upper and lower petals: Attenuate. Margin, upper and lower petals: Entire; not undulate. Texture and luster, upper and lower petals, upper and lower surfaces: Smooth, glabrous; slightly velvety; matte. Color, upper and lower petals: When opening, upper surface: Close to between 60B and 61B. When opening, lower surface: Close to 63B. Fully opened, upper surface: Close to 61B; venation, close to 61B; with development, color becoming closer to 63A. Fully opened, lower surface: Close to 70C; venation, close to 70C; color does not change with development.

*Sepals*.—Quantity and arrangement: Five, arranged in a single whorl. Length: About 2 mm. Width: About 1 mm. Shape: Ovate. Apex: Acute. Base: Broadly cuneate. Margin: Entire. Texture and luster, upper surface: Smooth, glabrous; matte. Texture and luster, lower surface: Smooth, glabrous; slightly glossy. Color: When opening, upper and lower surfaces: Close to 145A. Fully opened, upper and lower surfaces: Close to 144C.

*Peduncles*.—Length: About 19.1 cm. Diameter: About 3 mm. Aspect: About 10° from vertical; secondary peduncles, about 40° from main peduncle axis. Strength: Moderately weak. Texture and luster: Smooth, glabrous; moderately glossy. Color: Close to 176A; tinged on the shaded surface and towards the base, close to 152A.

*Pedicels*.—Length: About 1.4 cm. Diameter: About 0.5 mm. Aspect: About 30° from peduncle axis. Strength: Moderately strong. Texture and luster: Smooth, glabrous; slightly glossy. Color: Close to 152A to 152B.

*Reproductive organs*.—Stamens: Quantity per flower: About ten. Filament length: About 3.5 mm. Filament color: Close to N155C and 186C. Anther shape: Double reniform. Anther size: About 0.3 mm by 0.3 mm. Anther color: Close to N186C. Pollen amount: Sparse. Pollen color: Close to 29B to 29C. Pistils: Quantity per flower: About two, occasionally three. Pistil length: About 3 mm. Stigma diameter: About 0.2 mm. Stigma shape: Club-shaped. Stigma color: Close to 157A. Style length: About 3.8 mm. Style color: Close to 150C. Ovary color: Close to 150C. Floral bracts: Quantity per flower: One. Length: About 1.3 cm. Diameter: About 3 mm. Shape: Narrowly oblong to lanceolate. Apex: Broadly acute. Base: Broadly cuneate. Margin: Mostly entire. Color, upper surface: Darker than 147A; towards the base, close to 183A. Color, lower surface: Close to N199B; towards the base, close to 183A. Seeds and fruits: To date, seed and fruit development have not been observed on plants of the new *Saxifraga*.

Temperature tolerance: Plants of the new *Saxifraga* have been observed to tolerate temperatures ranging from about −7° C. to about 35° C. and to be suitable for USDA Hardiness Zones 8b through 11.

Pathogen & pest resistance: To date, plants of the new *Saxifraga* have not been observed to be resistant to pathogens and pests common to *Saxifraga* plants.

It is claimed:

1. A new and distinct *Saxifraga* plant named 'SH 1933' as illustrated and described.

* * * * *